(12) United States Patent
Fischer et al.

(10) Patent No.: US 6,359,178 B1
(45) Date of Patent: Mar. 19, 2002

(54) METHOD FOR PRODUCING HEXAMETHYLENE DIAMINE

(75) Inventors: Rolf Fischer, Heidelberg; Peter Bassler, Viernheim; Hermann Luyken, Ludwigshafen; Frank Ohlbach, Dossenheim; Johann-Peter Melder, Böhl-Iggelheim; Martin Merger, Frankenthal; Andreas Ansmann, Wiesloch; Alwin Rehfinger, Mutterstadt; Guido Voit, Freinsheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/762,798

(22) PCT Filed: Aug. 17, 1999

(86) PCT No.: PCT/EP99/06014

§ 371 Date: Feb. 13, 2001

§ 102(e) Date: Feb. 13, 2001

(87) PCT Pub. No.: WO00/12460

PCT Pub. Date: Mar. 9, 2000

(30) Foreign Application Priority Data

Aug. 28, 1998 (DE) .......................... 198 39 346

(51) Int. Cl.⁷ ............................................ C07C 209/48
(52) U.S. Cl. ........................................... 564/492
(58) Field of Search .......................... 564/792

(56) References Cited

U.S. PATENT DOCUMENTS

| 3,696,153 A | 10/1972 | Kershaw et al. ............ 260/583 |
| 4,064,172 A | 12/1977 | Dewdney et al. ............ 260/583 |
| 4,282,380 A | 8/1981 | Buehler et al. .............. 564/498 |
| 5,268,509 A | * 12/1993 | Immel et al. ................ 564/492 |
| 5,717,090 A | * 2/1998 | Bassler et al. .............. 540/539 |

FOREIGN PATENT DOCUMENTS

| WO | WO 98/11060 | 3/1998 |

OTHER PUBLICATIONS

McKetta Encyclopedia of Chemical Processing and Design, vol. 26 (1987), p. 230.

* cited by examiner

*Primary Examiner*—Brian J. Davis
(74) *Attorney, Agent, or Firm*—Keil & Weinkauf

(57) ABSTRACT

A process for catalytic hydrogenation of adiponitrile to hexamethylenediamine at elevated temperature and elevated pressure in the presence of catalysts based on elemental iron as catalytically active component and ammonia as solvent comprises a) hydrogenating adiponitrile at from 70 to 220° C. and from 100 to 400 bar in the presence of catalysts based on elemental iron as catalytically active component and ammonia as solvent to obtain a mixture comprising adiponitrile, 6-aminocapronitrile, hexamethylenediamine and high boilers until the sum total of the 6-aminocapronitrile concentration and the adiponitrile concentration is within the range from 1 to 50% by weight, based on the ammonia-free hydrogenation mixture, b) removing ammonia from the hydrogenation effluent, c) removing hexamethylenediamine from the remaining mixture, d) separating 6-aminocapronitrile and adiponitrile from high boilers individually or together, and e) returning 6-aminocapronitrile, adiponitrile or mixtures thereof into step a).

11 Claims, 1 Drawing Sheet

METHOD FOR PRODUCING HEXAMETHYLENE DIAMINE

BACKGROUND OF THE INVENTION

This invention relates to a process for catalytic hydrogenation of adiponitrile to hexamethylenediamine at elevated temperature and elevated pressure in the presence of catalysts based on elemental iron as catalytically active component and ammonia as solvent, which comprises a) hydrogenating adiponitrile at from 70 to 220° C. and from 100 to 400 bar in the presence of catalysts based on elemental iron as catalytically active component and ammonia as solvent to obtain a mixture comprising adiponitrile, 6-aminocapronitrile, hexamethylenediamine and high boilers until the sum total of the 6-aminocapronitrile concentration and the adiponitrile concentration is within the range from 1 to 50% by weight, based on the ammonia-free hydrogenation mixture, b) removing ammonia from the hydrogenation effluent, c) removing hexamethylenediamine from the remaining mixture, d) separating 6-aminocapronitrile and adiponitrile from high boilers individually or together, and e) returning 6-aminocapronitrile, adiponitrile or mixtures thereof into step a).

DESCRIPTION OF RELATED ART

U.S. Pat. No. 3,696,153 discloses hydrogenating adiponitrile to hexamethylenediamine at temperatures of 100 to 200° C. and pressures of about 340 atm in the presence of granulated catalysts comprising very predominantly iron and small amounts of aluminum oxide and in the presence of ammonia as solvent.

Hexamethylenediamine yields of 98.8%, 98.8%, 97.7% and 97.7% are reached in the examples of Table 1 (run 2) and Table 2 (runs 1 to 3) at pressures of 340 atm. Complete conversion is reported for the first three examples and 99.9% conversion for the fourth example. With regard to the life of the iron catalysts, Tables 1 and 2 merely reveal that catalyst activity is high at the end of the runs (after around 80 to 120 hours).

U.S. Pat. No. 4,064,172 discloses hydrogenating adiponitrile to hexamethylenediamine at pressures of 20 to 500 bar and temperatures of 80 to 200° C. in the presence of iron catalysts synthesized from magnetite and in the presence of ammonia. A hexamethylenediamine yield of 98.2% is reported in Example 1.

U.S. Pat. No. 4,282,381 describes the hydrogenation of adiponitrile to hexamethylenediamine with hydrogen at temperatures of 110 to 220° C. and a pressure of about 340 atm in the presence of ammonia and iron catalysts. The hydrogenation effluent contains 0.04 to 0.09% by weight of adiponitrile and 0.2 to 0.5% by weight of 6-aminocapronitrile.

McKetta, Encyclopedia of Chemical Processing and Design, Marcel Dekker Inc. 1987, volume 26, page 230, Table 3, confirms that a typical hydrogenation product contains 0.01 to 0.11% by weight of adiponitrile and 0.10 to 0.21% by weight of aminocapronitrile. Illustrations 2 and 4 reveal that these small aminocapronitrile quantities can be separated off and returned into the hydrogenation.

These processes suggest that the reaction conditions in the industrial production of hexamethylenediamine have to be directed to achieving complete conversion of the adiponitrile and of the 6-aminocapronitrile intermediate of the hydrogenation.

The disadvantage with this is that this requires a relatively high temperature and a very high reaction pressure. If the adiponitrile and 6-aminocapronitrile conversion decreases markedly in the course of the hydrogenation, it has to be pushed back up again by raising the temperature and optionally the reaction pressure and/or lowering the catalyst loading, or a not inconsiderable loss of product of value will be incurred.

If, to obtain complete conversion, the temperature cannot be further increased because of decreasing hexamethylenediamine selectivity and/or the pressure cannot be further increased for technical reasons, then the catalyst loading has to be reduced. However, this means that catalyst productivity, i.e., the amount of hexamethylenediamine produced per unit time, will decrease. If the productivity drops below a certain level, the hydrogenation plant has to be shut down and the iron catalyst moved and replaced with an unused or regenerated catalyst. The greater the frequency of such shutdowns required per year, the lower the hexamethylenediamine quantity which a given production plant can produce per year.

It is an object of the present invention to provide a process for the catalytic hydrogenation of adiponitrile to hexamethylenediamine in the presence of catalysts comprising very predominantly elemental iron and ammonia as solvent in an economical and technically simple manner while avoiding the disadvantages mentioned.

DETAILED DESCRIPTION OF THE INVENTION

The process of the invention does not require complete adiponitrile and 6-aminocapronitrile conversion. This provides distinctly higher catalysts onstream times at lower pressures, fewer shutdowns for the hydrogenation plant and hence distinctly higher hexamethylenediamine productivities compared with the prior art.

It was unforeseeable and hence it is surprising that recycling 6-aminocapronitrile, adiponitrile or mixtures thereof into the hydrogenation stage does not cause any shortening of the catalyst onstream time. It is also surprising that the entire recycle does not cause any troublesome buildup of by-products in the system.

The adiponitrile used in the process of the invention can generally be prepared by conventional processes, preferably by reaction of butadiene with hydrocyanic acid in the presence of catalysts, especially nickel (0) complexes and phosphorus-containing cocatalysts, via pentenenitrile as intermediate.

The catalysts used can be conventional iron catalysts known for the production of hexamethylenediamine by hydrogenation of adiponitrile. Preferred catalyst precursors are those which comprise from 90 to 100% by weight, preferably from 92 to 99% by weight, based on the total mass of the catalyst precursor, of iron oxides, iron(II, III) oxide, iron(II) oxide, iron(II) hydroxide, iron(III) hydroxide or iron oxyhydroxide such as FeOOH. It is possible to use synthetic or naturally occurring iron oxides, iron hydroxides or iron oxyhydroxides, magnetite, which has the idealized formula of $Fe_3O_4$, brown ironstone, which has the idealized formula of $Fe_2O_3 \times H_2O$, or hematite, which has the idealized formula of $Fe_2O_3$.

Preferred catalysts are those which comprise a) iron or a compound based on iron or mixtures thereof, b) from 0.001 to 5% by weight based on a) of a promoter based on 2, 3, 4, 5 or 6 elements selected from the group consisting of aluminum, silicon, zirconium, titanium, vanadium and manganese, and c) from 0 to 5% by weight based on a) of a compound based on an alkali metal or on an alkaline earth metal.

Further preferred catalyst precursors are those in which component b) comprises from 0.001 to 5% by weight, preferably from 0.01 to 4% by weight, especially from 0.1 to 3% by weight, of a promoter based on 2, 3, 4, 5 or 6 elements selected from the group consisting of aluminum, zirconium, silicon, titanium, manganese and vanadium.

Further preferred catalyst precursors are those in which component c) comprises from 0 to 5% by weight, preferably from 0.1 to 3% by weight, of a compound based on an alkali or alkaline earth metal preferably selected from the group consisting of lithium, sodium, potassium, rubidium, cesium, magnesium and calcium.

The catalysts can be supported or unsupported catalysts. Examples of suitable support materials are porous oxides such as aluminum oxide, silicon oxide, alumosilicates, lanthanum oxide, titanium dioxide, zirconium dioxide, magnesium oxide, zinc oxide and zeolites and also activated carbon or mixtures thereof.

Preparation is generally effected by precipitating precursors of component a) if desired together with precursors of the promoter components b) and if desired with precursors of the trace components c) in the presence or absence of support materials (depending on which type of catalyst is desired), if desired processing the resulting catalyst precursor into extrudates or tablets, drying and subsequently calcining. Supported catalysts are generally also obtainable by saturating the support with a solution of said components a), b) and if desired c), the individual components being added simultaneously or in succession, or by spraying said components a), if desired b) and c) onto the support in a conventional manner.

Suitable precursors for components a) are generally readily water-soluble salts of iron such as nitrates, chlorides, acetates, formates and sulfates, preferably nitrates.

Suitable precursors for components b) are generally readily water-soluble salts or complexes of the aforementioned metals and metalloids such as nitrates, chlorides, acetates, formates and sulfates, preferably nitrates.

Suitable precursors for components c) are generally readily water-soluble salts of the aforementioned alkali metals and alkaline earth metals such as hydroxides, carbonates, nitrates, chlorides, acetates, formates and sulfates, preferably hydroxides and carbonates.

Precipitation is generally effected from aqueous solutions, selectively by addition of precipitants, by changing the pH or by changing the temperature.

The catalyst prematerial thus obtained is usually dried, generally at from 80 to 150° C., preferably at from 80 to 120° C.

Calcination is customarily effected at temperatures within the range from 150 to 500° C., preferably from 200 to 450° C., in a gas stream comprising air or nitrogen.

After calcination, the catalyst material obtained is generally activated by exposing to a reducing atmosphere, for example by exposing it for from 2 to 100 hours to a hydrogen atmosphere or to a gas mixture comprising hydrogen and an inert gas such as nitrogen at from 200 to 500° C., preferably at from 250 to 400° C. The catalyst loading during this activating step is preferably 200 l per liter of catalyst.

The activation of iron catalysts by reduction of iron oxides with hydrogen can be carried out in a conventional manner, for example as described in U.S. Pat. No. 3,758,584, with mixtures of hydrogen and ammonia at from 300 to 600° C. or, as described in U.S. Pat. No. 4,480,051, in three steps, a first step of reducing the iron oxide with hydrogen or mixtures of hydrogen and ammonia, a second step of treating the resulting elemental iron with an oxygen-comprising gas, and then a third step of repeating the reduction of the first step.

U.S. Pat. No. 3,986,985 describes a deeper stabilization of reduced pyrophoric iron catalysts, for example in order that they may be transported. The original catalytic activity can be restored by a brief treatment of the stabilized catalyst with hydrogen.

The activation of the catalyst is advantageously carried out directly in the synthesis reactor, since this customarily dispenses with the otherwise necessary intermediary step, i.e., the passivation of the surface, customarily at from 20 to 80° C., preferably at from 25 to 35° C., by means of nitrogen-oxygen mixtures such as air. The activation of passivated catalysts is then preferably carried out in the synthesis reactor at from 180 to 500° C., preferably at from 200 to 400° C., in an atmosphere comprising hydrogen.

The catalysts may preferably be used as fixed bed catalysts in upflow or downflow mode or else as suspension catalysts.

The hydrogenation can be carried out batchwise, but is preferably carried out continuously using suspended, but preferably fixed bed, catalysts in the presence of ammonia.

Figure 1:
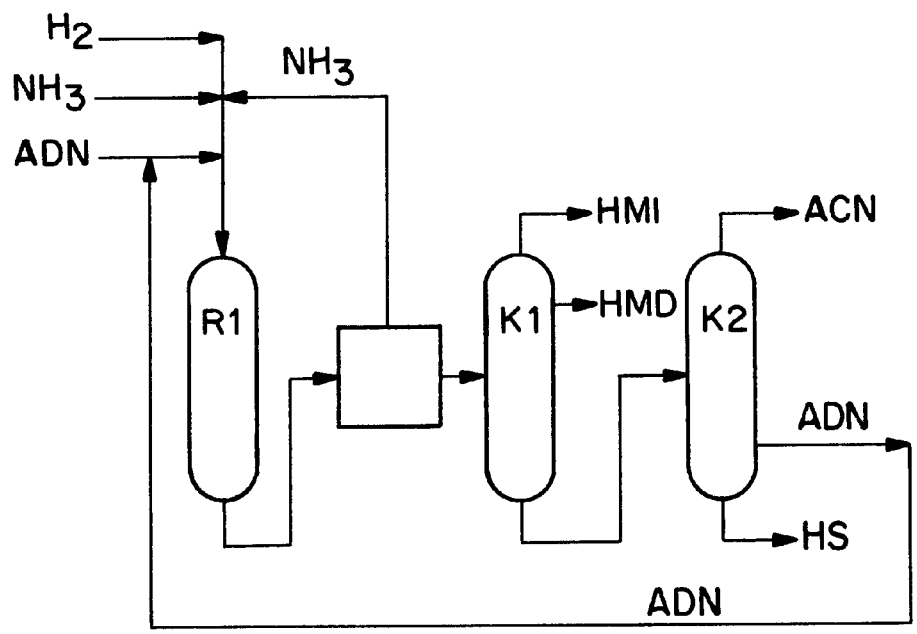
FIG. 1 is a diagramatic representation of a first embodiment of the process.
Figure 2:
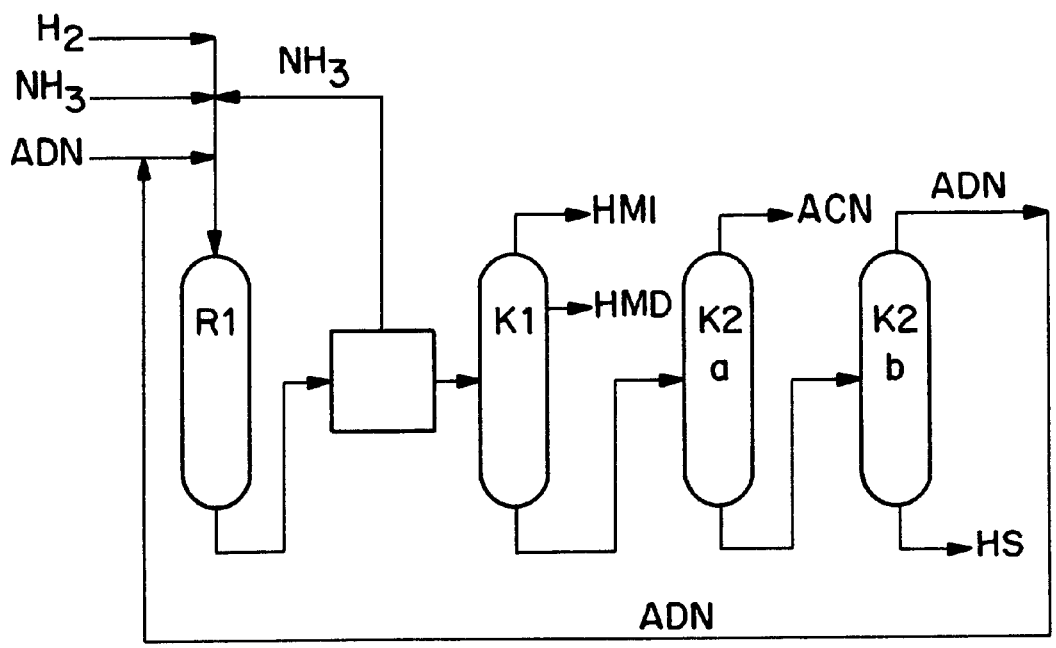
FIG. 2 is a diagramatic representation of a second embodiment of the process.

If fixed bed catalysts are used, the fixed bed reactor R 1 (see FIGS. 1 and 2) can be operated in downflow or upflow mode. It is possible in this connection to employ the operating mode of a straight pass through one reactor or through a plurality of consecutive reactors with or without intermediary cooling or an operating mode involving one or more reactors with product recycling in the liquid circulation system around the reactor(s).

The reaction temperature is generally within the range from 70 to 220° C., especially within the range from 80 to 170° C., and the pressure is generally within the range from 100 to 400 bar, especially within the range from 150 to 350 bar, particularly preferably within the range from 200 to 250 bar.

The catalyst loading is customarily within the range from 0.1 to 3 kg of adiponitrile/l of cat. x h, especially within the range from 0.5 to 2 kg of adiponitrilele of cat. x h.

The parameters, such as temperature, pressure and catalyst loading, for adjusting the sum total of the 6-aminocapronitrile concentration and the adiponitrile concentration, based on the ammonia-free hydrogenation mixture, in the reactor effluent to the range from 1 to 50% by weight, preferably 2–40% by weight, particularly preferably 3–40% by weight, especially 5–30% by weight, required by the invention can be easily determined by means of a few simple preliminary experiments.

The hydrogenation effluent of step a) has the ammonia removed from it in step b) in a conventional manner, preferably by distillation, for example as described in DE 19548289. The ammonia can then with advantage be reused in step a).

The mixture then has removed from it in a conventional manner, preferably by distillation, hexamethylenediamine and the by-produced hexamethyleneimine. In the case of a distillative removal, this can be accomplished in a plurality, such as two or three, columns or preferably one column K1.

The hexamethylenediamine obtained in step c) can then be purified in a conventional manner, preferably by distillation.

The product stream remaining after step c) comprises adiponitrile, 6-aminocapronitrile, by-products and compounds having a boiling point above that of adiponitrile ("high boilers"). These include nitrogen bases, such as 2-(5-cyanopentylamino)tetrahydroazepine and 2-(6-aminohexylamino)tetrahydroazepine. In step d), 6-aminocapronitrile and adiponitrile are removed from this product stream in a conventional manner, preferably by distillation, individually or together with high boilers. In the case of distillative removal, this can be accomplished in plural, such as two (K2 a and K2 b in FIG. 2) or three, columns or one column (K2 in FIG. 1). In the case of one column (K2), it is advantageous to obtain adiponitrile by sidestream takeoff, 6-aminocapronitrile overhead and high boilers as bottom product. Adiponitrile can be converted in the presence of the nitrogenous bases present in the bottom products, such as 2-(5-cyanopentylamino)tetrahydroazepine and 2-(6-aminohexylamino)tetrahydroazepine, into substantial amounts of 1-amino-2-cyanocyclopentene. Pure adiponitrile, in contrast, gives rise only to small amounts of 1-amino-2-cyclopentene at base of column temperatures of 200° C.

The 1-amino-2-cyanocyclopentene content, based on adiponitrile, in the adiponitrile used in step a), which comprises fresh adiponitrile and 6-aminocapronitrile, adiponitrile or mixtures thereof recycled from step e), should be below 5000 weight ppm, advantageously within the range from 10 to 5000 weight ppm, preferably within the range from 10 to 3000 weight ppm, particularly preferably within the range from 10 to 1500 weight ppm, especially within the range from 10 to 100 weight ppm.

Lowering the level of 1-amino-2-cyanocyclopentene content in the adiponitrile used in step a), which comprises fresh adiponitrile and 6-aminocapronitrile, adiponitrile or mixtures thereof recycled from step e), increases the yield of 6-aminocapronitrile and hexamethylenediamine and facilitates the purification of hexamethylenediamine.

In the case of a distillative removal, the base of column temperature should be advantageously below 220° C., preferably below 190° C., especially below 185° C., and because of the low vapor pressure of the compounds to be separated a base of column temperature of at least 100° C., preferably at least 140° C., especially at least 160° C., is advisable. The pressures at the base of the column should be advantageously within the range from 0.1 to 100, especially from 5 to 40, mbar. The residence times of the bottom products in the distillation should advantageously be within the range from 1 to 60, especially within the range from 5 to 15, minutes.

In a preferred embodiment, these distillation conditions are applied to the removal of adiponitrile from high boilers. In a preferred embodiment, the bottom product contains 1 to 80% by weight of adiponitrile, based on high boilers. Further adiponitrile may subsequently be obtained from this product stream, advantageously in an evaporator at a pressure of from 1 to 50 mbar, preferably from 2 to 25 mbar.

In step e), 6-aminocapronitrile, adiponitrile or mixtures thereof are returned into step a).

The present invention likewise proposes that hexamethylenediamine be removed, together with 6-aminocapronitrile, from the mixture obtained in step b) and then the mixture of hexamethylenediamine and 6-aminocapronitrile be separated into the two components.

In a further preferred embodiment, the adiponitrile stream to be returned into step a) has by-products, especially 1-amino-2-cyanocyclopentene, removed from it in a conventional manner, for example by distillation or extraction.

In a further preferred embodiment, the adiponitrile stream to be returned into step a) is purified in a conventional manner, for example by treatment with an inorganic acid, such as mineral acid, organic acid, such as carboxylic acid, or an acidic ion exchanger or by treatment with an oxidizing agent, such as air, ozone, hydrogen peroxide or an inorganic or organic peroxide.

The process of the present invention surprisingly provides distinct advantages with regard to the hydrogenation, the distillative purification of hexamethylenediamine and the onstream time of the hydrogenation catalyst.

We claim:

1. A process for catalytic hydrogenation of adiponitrile to hexamethylenediamine at elevated temperature and elevated pressure in the presence of a catalytically active elemental iron component and ammonia as solvent, which comprises
   a) hydrogenating adiponitrile at from 70 to 220° C. and from 100 to 400 bar in the presence of catalysts based on elemental iron as catalytically active component and ammonia as solvent to obtain a mixture comprising adiponitrile, 6-aminocapronitrile, hexamethylenediamine and high boilers until the sum total of the 6-aminocapronitrile concentration and the adiponitrile concentration is within the range from 1 to 50% by weight, based on the ammonia-free hydrogenation mixture,
   b) removing ammonia from the hydrogenation effluent,
   c) removing hexamethylenediamine from the remaining mixture,
   d) separating 6-aminocapronitrile and adiponitrile from high boilers individually or together, and
   e) returning 6-aminocapronitrile, adiponitrile or mixtures thereof into step a).

2. The process of claim 1, wherein the separating of the adiponitrile from high boilers is effected distillatively at base of column temperatures of below 220° C.

3. The process of claim 2, wherein the separating of the adiponitrile from high boilers is effected distillatively at base of column temperatures of below 185° C.

4. The process of claim 1, where in the separating of the adiponitrile from high boilers is effected distillatively and the high boilers stream obtained as bottom product is set to an adiponitrile content of from 1 to 80% by weight, based on the high boiler content.

5. The process of claim 4, wherein the main fraction of the adiponitrile in the stream of high boilers and adiponitrile is removed from the stream in a downstream evaporator at from 1 to 50 mbar.

6. The process of claim 1, which includes reducing the level of 1-amino-2-cyanocyclopentene by-product in the adiponitrile stream between steps d) and e).

7. The process of claim 1, further comprising treating the adiponitrile stream with an acid between steps d) and e).

8. The process of claim 7, wherein the acid used is a mineral acid, a carboxylic acid or an acidic ion exchanger.

9. The process of claim 1, further comprising treating the adiponitrile stream with an oxidizing agent between steps d) and e).

10. The process of claim 9, wherein the oxidizing agent used is air, ozone, hydrogen peroxide or an inorganic or organic peroxide.

11. The process of claim 1, wherein the 1-amino-2-cyanocyclopentene content of the adiponitrile used in step a) is below 5000 weight ppm based on adiponitrile.

* * * * *